US009765040B2

(12) United States Patent
Kiso et al.

(10) Patent No.: US 9,765,040 B2
(45) Date of Patent: Sep. 19, 2017

(54) THERAPEUTIC AGENT FOR PAIN

(75) Inventors: Tetsuo Kiso, Tokyo (JP); Mina Tsukamoto, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 13/820,873

(22) PCT Filed: Sep. 6, 2011

(86) PCT No.: PCT/JP2011/070205
§ 371 (c)(1),
(2), (4) Date: Mar. 5, 2013

(87) PCT Pub. No.: WO2012/033070
PCT Pub. Date: Mar. 15, 2012

(65) Prior Publication Data
US 2013/0165491 A1    Jun. 27, 2013

(30) Foreign Application Priority Data
Sep. 7, 2010 (JP) ................................. 2010-200305

(51) Int. Cl.
*C07D 249/08* (2006.01)
*C07D 403/04* (2006.01)
*A61K 31/4196* (2006.01)
*C07D 413/12* (2006.01)

(52) U.S. Cl.
CPC ........ *C07D 249/08* (2013.01); *A61K 31/4196* (2013.01); *C07D 403/04* (2013.01); *C07D 413/12* (2013.01)

(58) Field of Classification Search
CPC . C07D 249/08; C07D 403/04; A61K 31/4196
USPC ................. 514/383; 548/266.2, 268.2, 269.4
See application file for complete search history.

(56) References Cited

U.S. PATENT DOCUMENTS

| 8,377,923 B2 * | 2/2013 | Yoshimura et al. ..... 514/214.02 |
| 8,871,208 B2 * | 10/2014 | Jacobson et al. .......... 424/158.1 |
| 2004/0133011 A1 | 7/2004 | Waddell et al. |

FOREIGN PATENT DOCUMENTS

| CN | 101198605 A | 6/2008 |
| EP | 1790641 A1 | 5/2007 |
| EP | 1995243 A1 | 11/2008 |
| EP | 2298747 A1 | 3/2011 |
| JP | 2005170939 A | 6/2005 |
| WO | 03040110 A1 | 5/2003 |
| WO | 03104207 A2 | 12/2003 |
| WO | 03104208 A1 | 12/2003 |
| WO | 2004014881 A2 | 2/2004 |
| WO | 2004089470 A2 | 10/2004 |
| WO | 2005044192 A2 | 5/2005 |
| WO | 2005060963 A1 | 7/2005 |
| WO | 2005065683 A1 | 7/2005 |
| WO | 2006030805 A1 | 3/2006 |
| WO | 2006048750 A3 | 5/2006 |
| WO | 2006134467 A1 | 12/2006 |
| WO | 2006134481 A1 | 12/2006 |
| WO | 2007/021941 | 2/2007 |
| WO | 2007040982 A1 | 4/2007 |
| WO | 2007105753 A1 | 9/2007 |
| WO | 2010001946 A1 | 1/2010 |
| WO | 2011068927 A2 | 6/2011 |

OTHER PUBLICATIONS

Captain David Williams: Vicious Circle Theory of Chronic Fatigue Syndrome and Fibromyalgia, Jul. 1999 (Jul. 1999), XP002718138, Retrieved from the Internet: URL:http://www.newtreatments.org/fromweb/1icoriceprotocol.txt, total 20 pages.
Communication from the European Patent Office issued Jan. 14, 2014 in a counterpart European Application No. 11823545.6.
Staab, Claudia A., et al., "11β-Hydroxysteroid dehydrogenase type 1 is an important regulator at the interface of obesity and inflammation", Journal of Steroid Biochemistry and Molecular Biology, vol. 119, 2010, pp. 56-72.
Woolf, Clifford J., et al., "Neuropathic pain: aetiology, symptoms, mechanisms, and management", The Lancet, vol. 353, Jun. 5, 1999, pp. 1959-1964.
Sindrup, Soren H., et al., "Antidepressants in the Treatment of Neuropathic Pain", Basic & Clinical Pharmacology & Toxicology, vol. 96, 2005, pp. 399-409.
Pappagallo MD, Marco, "Newer Antiepileptic Drugs: Possible Uses in the Treatment of Neuropathic Pain and Migraine", Clinical Therapeutics, vol. 25, No. 10, 2003, pp. 2506-2538.
Wolfe, Frederick, et al., "The American College of Rheumatology 1990 Criteria for the Classification of Fibromyalgia", Arthritis and Rheumatism, vol. 33, No. 2, Feb. 1990, pp. 160-172.
Mease, Philip J., et al., "A Randomized, Double-blind, Placebo-Controlled, Phase III Trial of Pregabalin in the Treatment of Patients with Fibromyalgia", The Journal of Rheumatology, vol. 35, No. 3, 2008, pp. 502-514.
Russell, I. John, et al., "Efficacy and Safety of Duloxetine for Treatment of Fibromyalgia in Patients With or Without Major Depressive Disorder: Results from a 6-month, Randomized, Double-blind, Placebo-controlled, Fixed-dose Trial", International Association for the Study of Pain, vol. 136, 2008, pp. 432-444.

(Continued)

*Primary Examiner* — Irina Neagu
(74) *Attorney, Agent, or Firm* — Oblon, McClelland, Maier & Neustadt, L.L.P.

(57) ABSTRACT

[Problem]
Provided is a pharmaceutical, in particular, a pharmaceutical composition which is useful for the treatment of pain.
[Means for Solution]
The present inventors have made extensive studies using model animals with pain for the purpose of providing a therapeutic agent for pain. As a result, they have found that 11β-hydroxydehydrogenase type 1 (11β-HSD1) inhibitor, in particular, a triazole compound having a cyclic group at the 3-position (or 5-position) of a triazole ring has a good effect of ameliorating chronic pain. That is, according to the present invention, a pharmaceutical composition comprising an 11β-HSD1 inhibitor, in particular, the triazole compound of the present invention, as an active ingredient, is useful for the treatment of pain (particularly, neuropathic pain or fibromyalgia).

9 Claims, No Drawings

(56) References Cited

OTHER PUBLICATIONS

Holman, Andrew J., et al., "A Randomized, Double-Blind, Placebo-Controlled Trial of Pramipexole, a Dopamine Agonist, in Patients With Fibromyalgia Receiving Concomitant Medications", Arthritis & Rheumatism, vol. 52, No. 8, Aug. 2005, American College of Rheumatology, pp. 2495-2505.
Odermatt, Alex, at al., "The Glucocorticoid-activating Enzyme 11β-Hydroxysteroid Dehydrogenase type 1 has Broad Substrate Specificity: Physiological and Toxicological Considerations", Journal of Steroid Biochemistry & Molecular Biology, vol. 119, 2010, pp. 1-13.
Morton, Nicholas M., et al., "Improved Lipid and Lipoprotein Profile, Hepatic Insulin Sensitivity, and Glucose Tolerance in 11β-Hydroxysteroid Dehydrogenase Type 1 Null Mice", The Journal of Biological Chemistry, vol. 276, No. 44, Nov. 2, 2001, pp. 41293-41300.
Davani, Behrous, et al., "Type 1 11β-Hydroxysteroid Dehydrogenase Mediates Glucorticoid Activation and Insulin Release in Pancreatic Islets", The Journal of Biological Chemistry, vol. 275, No. 45, Nov. 10, 2000, pp. 34841-34844.
Moisan, Marie-Pierre, et al., "11β-Hydroxysteroid Dehydrogenase Bioactivity and Messenger RNA Expression in Rat Forebrain: Localization in Hypothalamus, Hippocampus, and Cortex", Endocrinology, vol. 127, No. 3, 1990, pp. 1450-1455.
Sandeep, Thekkepat C., et al., "11β-Hydroxysteroid Dehydrogenase Inhibition Improves Cognitive Function in Healthy Elderly Men and Type 2 Diabetics", Proceeding of the National Academy of Science, vol. 101, No. 17, Apr. 27, 2004, pp. 6734-6739.
Yau, Joyce L. W., et al., "Lack of Tissue Glucocorticoid Reactivation in 11β-Hydroxysteroid Dehydrogenase Type 1 Knockout Mice Ameliorates Age-related Learning Impairments", Proceeding of the National Academy of Science, vol. 98, No. 8, Apr. 10, 2001, pp. 4716-4721.
International Search Report dated Nov. 15, 2011 issued by the International Searching Authority in counterpart International Application No. PCT/JP2011/070205.
Written Opinion dated Nov. 15, 2011 issued by the International Searching Authority in counterpart International Application No. PCT/JP2011/070205.
Woolf et al, "Neuropathic pain: aetiology, symptoms, mechanisms, and management", Lancet, 1999, vol. 353, pp. 1959-1964.
Yunis et al, "Short Term Effects of Ibuprofen in Primary Fibromyalgia Syndrome: A Double Blind, Placebo Controlled Trial", Journal of Rheumatology, 1989, vol. 16, No. 4, pp. 527-532.
Skaer, "Fibromyalgia: Disease Synopsis, Medication Cost Effectiveness and Economic Burden", PharmacoEconomics, (2014) vol. 32, pp. 457-466.
Combined Chinese Office Action and Search Report issued Jan. 20, 2014 in Patent Application No. 201180042963.2 (with English language translation).
Combined Chinese Office Action and Search Report issued Sep. 26, 2014 in Patent Application No. 201180042963.2 (with English language translation).
Israelite Office Action issued Sep. 21, 2014 in Patent Application No. 224920 (English Translation only).
Australian Office Action issued May 23, 2014 in Patent Application No. 2011299905.
Decision of Rejection issued on Apr. 22, 2015 in the corresponding Chinese Patent Application No. 201180042963.2 and English translation.
Office Action issued on Jun. 2, 2015 in the corresponding Japanese Patent Application No. 2012-532977 and English translation.
C.J. Woolf et al., The Lancet, vol. 353, pp. 1959-1964 (1999).
Indonesian Office Action issued Sep. 7, 2015 in Patent Application No. W00201300976 (with English translation).
Office Action issued Nov. 12, 2015 in Ukrainian Patent Application No. 2013 04329 (with English language translation).
Office Action issued Feb. 6, 2017 in Canadian Patent Application No. 2809778.
Notification of Reexamination dated Jan. 27, 2016 issued in corresponding Chinese Patent Application No. 201180042963.2 (with English translation ).
Decision on Reexamination issued Jun. 13, 2016, in Chinese Patent Application No. 201180042963.2, filed Mar. 5, 2013 (with English-language Translation).
Notice of Preliminary Rejection issued Jan. 19, 2017, in Korean patent application No. 10-2013-7008722 (w/English translation).
Combined Taiwanese Office Action and Search Report dated Oct. 23, 2014 in Patent Application No. 100132078 with English Translation and English Translation of Category of Cited Documents.

* cited by examiner

THERAPEUTIC AGENT FOR PAIN

This application is a National Stage entry of International Application No. PCT/JP2011/070205, filed on Sep. 6, 2011, which claims the benefit of priority to Japanese Patent Application No. 2010-200305, filed on Sep. 7, 2010.

TECHNICAL FIELD

The present invention relates to a pharmaceutical composition which is useful as a therapeutic agent for pain, in particular, neuropathic pain or fibromyalgia.

BACKGROUND ART

There are various classifications of pain, but in terms of the duration or nature, they may be classified into acute pain which plays a role as a biological alert system and chronic pain in which a duration taken for curing the diseases is exceeded usually but complaints of pain continue. According to the causes, pain can be classified into three main types, that is, nociceptive pain, neuropathic pain, and psychogenic pain. Neuropathic pain refers to intractable chronic pain which occurs as a result of dysfunction of the peripheral or central nervous system. Typical examples of neuropathic pain include pain associated with diabetic neuropathy, postherpetic neuralgia, low back pain and leg pain, trigeminal neuralgia, cancer pain, post-operative or post-traumatic prolonged pain, pain induced by spinal cord injury, thalamic pain, multiple sclerosis-derived pain, a complex regional pain syndrome (CRPS), phantom limb pain, HIV-related neuropathic pain, and the like. There are many unclear points about the onset mechanism of the disease, but believed to be induced by persistent abnormal firing of sensory nerves or the like. Typical examples of neuropathic pain include allodynia, hyperalgesia, hyperesthesia, and the like. These symptoms exhibit characteristic pain which is expressed by "burning", "pins and needles", "electric shock-like", or the like.

It is known that non-steroidal anti-inflammatory analgesics which are effective for common nociceptive pain are ineffective for neuropathic pain, and even narcotic analgesics such as morphine and the like do not work well for neuropathic pain (Non-Patent Document 1). As a treatment method for neuropathic pain, neurosurgical treatments such as nerve block, electrical stimulation of spinal epidural, and the like, an antidepressant (Non-Patent Document 2), an antiepileptic (Non-Patent Document 3), and the like have been used, but a safe and effective treatment method has not been established. In recent years, new drugs such as pregabalin which is a ligand for an α2δ subunit of a voltage-dependent calcium channel have been launched commercially, but their efficacy rates are not so high and there are problems in side effects such as sleepiness, dizziness, and the like. Since a safe and effective treatment method for neuropathic pain has not been still established, there is a strong demand for development of a superior therapeutic agent having fewer side effects with sufficient efficacy.

Fibromyalgia has a core symptom of unbearable chronic pain throughout the whole body, and is a chronic pain disease accompanied by a variety of associated symptoms such as insomnia, systemic fatigue, depressive symptoms, and the like. The symptoms of fibromyalgia are very diverse. The pain symptoms of fibromyalgia are characterized by being accompanied by chronic pain in deep tissues such as muscle tissues, and pain during finger pressure massage. Further, fibromyalgia is often associated with allodynia such as touch allodynia and cold allodynia, or thermal hyperalgesia. Further, as compared with patients with other pain diseases (neuropathic pain, rheumatoid arthritis, osteoarthritis, acute pain after operation, and the like), patients with fibromyalgia have higher rates of being associated with accompanying symptoms including affective disorders such as depression, anxiety, and the like, feeling of fatigue, sleep disorders, irritable bowel syndrome, and the like. For other pain diseases, organic disorder or functional disorder which causes pain are clear to certain degrees, whereas for the patients with fibromyalgia, the causes accounting for pain are not clear. In accordance with the American College of Rheumatology, diagnostic criteria for fibromyalgia is defined as history of widespread pain lasting for at least three months, and pain being present in at least 11 of 18 tender point sites in the whole body (ligaments, tendon, muscles, and the like in contact with the bones) (Non-Patent Document 4). These diagnostic criteria are clearly different from those of other pain diseases. That is, fibromyalgia is a chronic disease which is independently present and clearly different from other pain diseases from the viewpoints of symptoms, causes of pain, diagnostic criteria, and the like.

In recent years, agents including pregabalin (Non-Patent Document 5), duloxetine which is an SNRI (serotonin- and noradrenaline-reuptake inhibitor) (Non-Patent Document 6), pramipexole which is a dopamine agonist (Non-Patent Document 7), and the like have been reported to statistically significantly reduce the pain symptom scores of patients with fibromyalgia, as compared with a placebo group, but the effects of these agents are limited. A safe and effective treatment method for fibromyalgia has yet to be established, and therefore, there is a strong demand for development of a superior therapeutic agent having fewer side effects with sufficient efficacy.

Glucocorticoid is a hormone which causes metabolic disorders such as hyperglycemia, insulin resistance, obesity, hyperlipidemia, hypertension and the like, and is not only produced from adrenal glands but also converted from the inactive form into the active form at the tissue level, and acts via its receptor.

11β-Hydroxysteroid dehydrogenase (11β-HSD) is an enzyme which catalyzes this conversion and the presence of two subtypes thereof is known. 11β-Hydroxysteroid dehydrogenase type 1 (11β-HSD1) is an enzyme which converts the inactive form into the active form and highly expressed in the liver, and 11β-hydroxysteroid dehydrogenase type 2 (11β-HSD2) is an enzyme which converts the active form into the inactive form and highly expressed in the kidney. 11β-HSD1 has a wide range of substrate specificity (Non-Patent Document 8), but the relation thereof with glucocorticoid is most well-known. Since it has been reported, for example, that an 11β-HSD1 knockout mouse exhibits improved glucose tolerance, lowered blood triglyceride, and increased HDL-cholesterol (Non-Patent Document 9) and a non-selective 11β-HSD inhibitor, carbenoxolone, improves the lowering of insulin secretion in mouse pancreatic β-cell caused by the addition of inactive-form glucocorticoid (Non-Patent Document 10), it is expected that an 11β-HSD1 selective inhibitor inhibits the conversion into active-form glucocorticoid, and thus inhibits the glucocorticoid action in the tissues, and as a result, metabolic abnormalities such as hyperglycemia, insulin resistance, obesity, hyperlipidemia, hypertension, and the like induced by glucocorticoid, are cured (Patent Document 1).

11β-HSD1 is also expressed in the central nervous system such as the brain and the spinal cord (Non-Patent Documents 11 and 12). Since an action of improving language memory by administering a nonselective 11β-HSD inhibitor to a patient with type II diabetes (Non-Patent Document 12), and an action of ameliorating cognition disorders in aged 11β-HSD1 knockout mice (Non-Patent Document 13), and the like have been reported, it is expected that the 11β-HSD1-selective inhibitor inhibits the action of glucocorticoid in the brain through the inhibition of conversion into an active-form glucocorticoid, and as a result, cognition disorders induced by glucocorticoid is cured (Patent Document 1). The 11β-HSD1 inhibitor is also expected to have an effect to ameliorate, in addition to dementia, diseases in the central nervous system, such as schizophrenia, depression, anxiety, post-traumatic stress disorder (PTSD), attention deficit/hyperactivity disorder (AD/HD), panic disorder, somnipathy, and the like, which are greatly related to stress and in which an HPA axis disorder, an increase in cortisol in the blood plasma, or the like is recognized.

As for other diseases in which 11β-HSD1 is involved, osteoporosis and glaucoma are known, and the ameliorating effects by the 11β-HSD1 inhibitor on these diseases are expected.

While the involvement of 11β-HSD1 is known in a number of these diseases, the involvement of 11β-HSD1 in pain has not been clearly known, and in addition, the therapeutic effect of the 11β-HSD1 inhibitor for pain has been unexplained thus far.

As the 11β-HSD1 inhibitor, for example, there are reports of Patent Documents 1 to 11.

In Patent Document 1, it is described that a triazole compound represented by the following general formula (A) has an 11β-HSD1 inhibitory action and is useful for the treatment of diseases such as diabetes, hyperglycemia, insulin resistance, obesity, hyperlipidemia, hypertension, osteoporosis, glaucoma, dementia, schizophrenia, depression, and the like. However, there is no description of usefulness for the treatment of pain.

[Chem. 1]

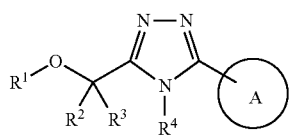

(A)

(Refer to this publication for the symbols in the formula.)

In Patent Document 2, it is described that a triazole compound represented by the following general formula (B) has an 11β-HSD1 inhibitory action and is useful for the treatment of diseases such as diabetes, hyperglycemia, obesity, insulin resistance, dyslipidemia, hyperlipidemia, hypertension, a metabolic syndrome, and the like. However, there is no description of usefulness for the treatment of pain.

[Chem. 2]

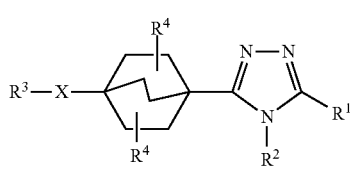

(B)

(Refer to this publication for the symbols in the formula)

In Patent Documents 3 and 4, it is described that a triazole compound represented by the following general formula (C) has an 11β-HSD1 inhibitory action and is useful for the treatment of diseases such as diabetes, hyperglycemia, hypertension, obesity, insulin resistance, dyslipidemia, hyperlipidemia, hypertension, an X syndrome, and the like. However, there is no description of usefulness for the treatment of pain.

[Chem. 3]

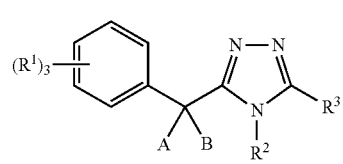

(C)

(Refer to this publication for the symbols in the formula.)

In Patent Document 5, it is described that a triazole compound represented by the following general formula (D) has an 11β-HSD1 inhibitory action and is useful for the treatment of diseases such as diabetes, obesity, and a metabolic syndrome. However, there is no description of usefulness for the treatment of pain.

[Chem. 4]

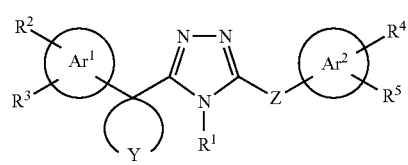

(D)

(Z in the formula represents —(CH($R^{14}$))p-, —(CH($R^{14}$))p-N($R^{16}$)—(CH($R^{15}$))q-, or

[Chem. 5]

Refer to this publication for other symbols.)

In Patent Document 6, it is described that a triazole compound represented by the following general formula (E) has an 11β-HSD1 inhibitory action and is useful for the treatment of diseases such as diabetes, hyperglycemia, insulin resistance, obesity, hyperlipidemia, hypertension, osteoporosis, glaucoma, lowering of cognitive function, and the like. However, there is no description of usefulness for the treatment of pain.

[Chem. 6]

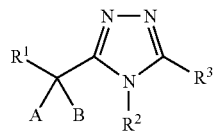

(E)

(Refer to this publication for other symbols in the formula.)

In Patent Document 7, it is described that a triazole compound represented by the following general formula (F) has an 11β-HSD1 inhibitory action and is useful for the treatment of diseases such as diabetes, hyperglycemia, insulin resistance, obesity, hyperlipidemia, hypertension, osteoporosis, glaucoma, lowering of cognitive function, and the like. However, there is no description of usefulness for the treatment of pain.

[Chem. 7]

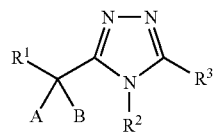

(F)

(In the formula, $R^1$ represents a heterocyclic group or $—N(R^0)—R^4$, and A and B represent lower alkyl, or a cycloalkyl ring formed by the combination with carbon atoms to which these are bonded. Refer to this publication for other symbols.)

In Patent Document 8, it is described that a compound represented by the following general formula (G) has an 11β-HSD1 inhibitory action and is useful for the treatment of diabetes, metabolic syndrome, insulin resistance, obesity, glaucoma, hyperglycemia, hyperinsulinemia, osteoporosis, tuberculosis, atherosclerosis, dementia, depression, virus diseases, inflammatory disease, and diseases in which the liver is a target organ. Further, there is a description of pain for lots of diseases exemplified as an inflammatory disease, but there is no description of neuropathic pain.

[Chem. 8]

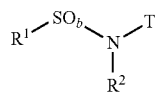

(G)

(Refer to this publication for other symbols in the formula.)

In Patent Document 9, it is described that a compound represented by the following general formula (H) has an 11β-HSD1 inhibitory action and is useful for the treatment of diabetes, metabolic syndrome, insulin resistance, obesity, glaucoma, hyperglycemia, hyperinsulinemia, osteoporosis, atherosclerosis, dementia, depression, virus disease, inflammatory disease, and diseases in which the liver is a target organ. Further, there is a description of pain for lots of diseases exemplified as an inflammatory disease, but there is no description of neuropathic pain.

[Chem. 9]

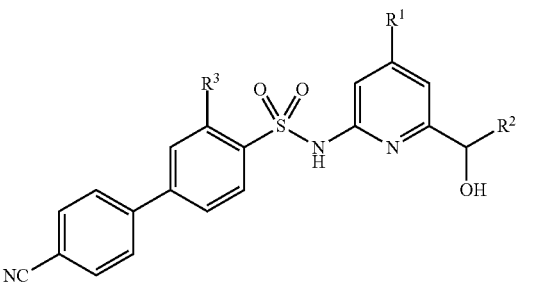

(H)

(Refer to this publication for other symbols in the formula.)

In Patent Document 10, it is described that a compound represented by the following general formula (J) has an 11β-HSD1 inhibitory action and is useful for the treatment of diabetes, metabolic syndrome, insulin resistance, obesity, glaucoma, hyperglycemia, hyperinsulinemia, osteoporosis, atherosclerosis dementia, depression, virus disease, inflammatory disease, and diseases in which the liver is a target organ. Further, there is a description of pain for lots of diseases exemplified as an inflammatory disease, but there is no description of neuropathic pain.

[Chem. 10]

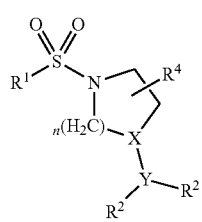

(J)

(Refer to this publication for other symbols in the formula.)

In Patent Document 11 which has been published after the priority date of the present application, it is described that an 11β-HSD1 inhibitor such as a compound represented by the following general formula (K) and the like is useful for the treatment of inflammation, chronic inflammation, pain, rheumatoid arthritis (RA), or osteoarthritis (OA), and as specific examples of the pain, pain associated with neuropathic pain and fibromyalgia, and the like are described. However, in Patent Document 11, a test method for neuropathic pain is described, but there is no disclosure of any test results for neuropathic pain and pain accompanied by fibromyalgia is described only in one line.

[Chem. 11]

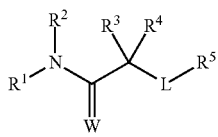

(K)

(Refer to this publication for other symbols in the formula.)

RELATED ART

Patent Documents

Patent Document 1: Pamphlet of International Publication WO 2010/001946
Patent Document 2: Specification of U. S. Publication No. 2004/0133011
Patent Document 3: Pamphlet of International Publication WO 03/104207
Patent Document 4: Pamphlet of International Publication WO 03/104208
Patent Document 5: Pamphlet of International Publication WO 2005/044192
Patent Document 6: Pamphlet of International Publication WO 2006/030805
Patent Document 7: Pamphlet of International Publication WO 2007/105753
Patent Document 8: Pamphlet of International Publication WO 2005/060963
Patent Document 9: Pamphlet of International Publication WO 2006/134467
Patent Document 10: Pamphlet of International Publication WO 2006/134481
Patent Document 11: Pamphlet of International Publication WO 2011/068927

Non-Patent Documents

Non-Patent Document 1: Lancet, 1999, Vol. 353, p. 1959-1966
Non-Patent Document 2: Basic & Clinical Pharmacology & Toxicology, 2005, Vol. 96, p. 399-409
Non-Patent Document 3: Clinical Therapeutics, 2003, Vol. 25, p. 2506-2538
Non-Patent Document 4: Arthritis & Rheumatism, 1990, Vol. 33, p. 160-172
Non-Patent Document 5: Journal of Rheumatology, 2008, Vol. 35, p. 502-514
Non-Patent Document 6: Pain, 2008, Vol. 136, p. 432-444
Non-Patent Document 7: Arthritis & Rheumatism, 2005, Vol. 52, p. 2495-2505
Non-Patent Document 8: Journal of Steroid Biochemistry & Molecular Biology, 2010, 119, p. 1-13
Non-Patent Document 9: Journal of Biological Chemistry, 2001, Vol. 276, p. 41293-41300
Non-Patent Document 10: Journal of Biological Chemistry, 2000, Vol. 275, p. 34841-34844
Non-Patent Document 11: Endocrinology, 1990, Vol. 127, p. 1450-1455
Non-Patent Document 12: Proceeding of the National Academy of Science, 2004, Vol. 101, p. 6734-6739
Non-Patent Document 13: Proceeding of the National Academy of Science, 2001, Vol. 98, p. 4716-4721

DISCLOSURE OF INVENTION

Problems to be Solved by the Invention

An object of the present invention is to provide medicine which is useful for the treatment of pain (in particular, neuropathic pain or fibromyalgia).

Means for Solving the Problems

The present inventors have made extensive studies using model animals with pain for the purpose of providing a therapeutic agent for pain. As a result, they have found that a compound having an 11β-HSD1 inhibitory activity, in particular, a triazole compound having a cyclic group at the 3-position (or 5-position) of a triazole ring has a good chronic pain-ameliorating effect, thereby completing the present invention.

That is, the present invention relates to:

(1) a therapeutic agent for pain comprising a compound represented by the formula (I-a) or a pharmaceutically acceptable salt thereof as an active ingredient:

[Chem. 12]

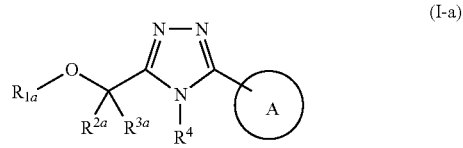

(I-a)

[the symbols in the formula have the following meanings:
Ring A: aryl, heterocyclic group, or cycloalkyl, each of which may be substituted,
$R^{1a}$: aryl or heterocyclic group each of which may be substituted, or lower alkylene-cycloalkyl,
$R^{2a}$: lower alkyl,
$R^{3a}$: —H or lower alkyl, or
$R^{2a}$ and $R^{3a}$ are combined with each other to form $C_{2-6}$ alkylene, and
$R^4$: lower alkyl, halogeno-lower alkyl, lower alkylene-O-lower alkyl, cycloalkyl, lower alkylene-S-lower alkyl, lower alkylene-S(O)-lower alkyl, lower alkylene-S(O)$_2$-lower alkyl, or lower alkylene-cycloalkyl (the same shall apply hereinafter)];

(2) the therapeutic agent for pain as set forth in (1), wherein the pain is neuropathic pain; and (3) the therapeutic agent for pain as set forth in (1), wherein the pain is fibromyalgia.

The present invention further relates to use of the compound of the formula (I-a) or a pharmaceutically acceptable salt thereof for the manufacture of a pharmaceutical composition for preventing or treating pain (in particular, neuropathic pain or fibromyalgia), the compound of the formula (I-a) or a salt thereof used for the treatment of pain (in particular, neuropathic pain or fibromyalgia), and a method for treating pain, including a step of administering an effective amount of the compound of the formula (I-a) or a salt thereof to a subject.

That is, the present invention relates to:

(4) use of the compound represented by the formula (I-a) or a pharmaceutically acceptable salt thereof for the manufacture of a therapeutic agent for pain;

(5) use of the compound represented by the formula (I-a) or a pharmaceutically acceptable salt thereof for the treatment of pain;

(6) the compound represented by the formula (I-a) or a pharmaceutically acceptable salt thereof for the treatment of pain; and (7) a method for treating pain, comprising a step of administering a therapeutically effective amount of the compound represented by the formula (I-a) or a pharmaceutically acceptable salt thereof to a patient.

The present invention further relates to:

(8) a therapeutic agent for fibromyalgia comprising an 11β-HSD1 inhibitor as an active ingredient.

EMBODIMENTS FOR CARRYING OUT THE INVENTION

Hereinafter, the present invention will be described in detail.

The "lower alkyl" is preferably linear or branched alkyl having 1 to 6 carbon atoms (hereinafter abbreviated as $C_{1-6}$), specifically methyl, ethyl, n-propyl, isopropyl, n-butyl, isobutyl, sec-butyl, tert-butyl, n-pentyl, n-hexyl, or the like, more preferably $C_{1-4}$ alkyl, and particularly preferably methyl, ethyl, n-propyl, or isopropyl.

The "lower alkylene" is preferably linear or branched $C_{1-6}$ alkylene, specifically, methylene, ethylene, trimethylene, tetramethylene, pentamethylene, hexamethylene, propylene, methylmethylene, ethylethylene, 1,2-dimethylethylene, 1,1,2,2-tetramethylethylene, or the like, more preferably, $C_{1-4}$ alkylene, and particularly preferably methylene, ethylene, or trimethylene.

The "halogen" means F, Cl, Br, or I.

The "halogeno-lower alkyl" is lower alkyl substituted with one or more halogen atoms, preferably lower alkyl substituted with 1 to 7 halogen atoms, more preferably lower alkyl substituted with 1 to 5 halogen atoms, and still more preferably fluoromethyl, difluoromethyl, or trifluoromethyl.

The "halogeno-lower alkylene" is lower alkylene substituted with one or more halogen atoms, preferably lower alkylene substituted with 1 to 7 halogen atoms, and more preferably fluoromethylene, difluoromethylene, trifluoromethylmethylene, or bistrifluoromethylmethylene.

The "cycloalkyl" is a $C_{3-10}$ saturated hydrocarbon ring group, which may have a bridge, specifically, cyclopropyl, cyclobutyl, cyclopentyl, cyclohexyl, cycloheptyl, cyclooctyl, adamantyl, or the like, preferably $C_{3-8}$ cycloalkyl, and more preferably cyclopropyl, cyclobutyl, cyclopentyl, or cyclohexyl.

The "cycloalkenyl" is $C_{3-15}$ cycloalkenyl, which may have a bridge and includes a cyclic group fused with a benzene ring in a moiety with a double bond, specifically, a cyclopentenyl, cyclopentadienyl, cyclohexenyl, cyclohexadienyl, 1-tetrahydronaphthyl, 1-indenyl, 9-fluorenyl, or the like, more preferably $C_{5-10}$ cycloalkenyl, and particularly preferably cyclopentenyl or cyclohexenyl.

The "aryl" is a $C_{6-14}$ monocyclic to tricyclic aromatic hydrocarbon ring group, preferably phenyl or naphthyl, and more preferably phenyl.

The "heterocyclic" group means a cyclic group of i) a monocyclic 3- to 8-membered (preferably 5- to 7-membered) heterocycle having 1 to 4 hetero atoms selected from O, S, and N, or ii) a bicyclic 8- to 14-membered (preferably 9- to 11-membered) heterocycle or a tricyclic 11- to 20-membered (preferably 12- to 15-membered) heterocycle having 1 to 5 hetero atoms selected from O, S, and N, which is formed by the ring fusion of the monocyclic heterocycle with one or two rings selected from the group consisting of a monocyclic heterocycle, a benzene ring, a $C_{5-8}$ cycloalkane, and a $C_{5-8}$ cycloalkene. The ring atom, S or N, may be oxidized to form an oxide or a dioxide. The "heterocyclic" group is preferably aziridinyl, azetidyl, pyrrolidinyl, piperidinyl, piperazinyl, homopiperazinyl, oxiranyl, oxetanyl, tetrahydrofuranyl, tetrahydropyranyl, morpholinyl, homomorpholinyl, tetrahydrothiopyranyl, pyrrolyl, pyrazolyl, imidazolyl, triazolyl, tetrazolyl, pyridyl, pyrimidinyl, pyrazinyl, furyl, thienyl, oxazolyl, isoxazolyl, oxadiazolyl, thiazolyl, isothiazolyl, thiadiazolyl, indolyl, isoindolinyl, indazolyl, indolizinyl, benzimidazolyl, imidazo[1,2-a]pyridinyl, quinoxalinyl, quinolyl, isoquinolyl, quinazolyl, cinnonyl, phthalazyl, benzofuranyl, benzothienyl, benzoxazolyl, benzothiazolyl, benzotriazolyl, 4,5,6,7-tetrahydroindazolyl, 4,5,6,7-tetrahydropyrazolo[4,3-c]pyridinyl, 4,5,6,7-tetrahydrobenzimidazolyl, carbazolyl, or quinuclidinyl, more preferably a monocyclic heterocyclic group, and still more preferably pyrrolidinyl, piperidinyl, piperadinyl, morpholinyl, pyridyl, pyrimidinyl, oxazolyl, isoxazolyl, oxadiazolyl, or thiazolyl.

The "heteroaryl" means an aromatic heterocyclic ring among the "heterocyclic" groups above, specifically, pyrrolyl, pyrazolyl, imidazolyl, triazolyl, tetrazolyl, pyridyl, pyrimidinyl, pyrazinyl, furyl, thienyl, oxazolyl, isoxazolyl, oxadiazolyl, thiazolyl, isothiazolyl, thiadiazolyl, indolyl, indazolyl, benzimidazolyl, imidazo[1,2-a]pyridinyl, quinoxalinyl, quinolyl, isoquinolyl, quinazolyl, cinnonyl, phthalazyl, benzofuranyl, benzothienyl, benzoxazolyl, benzothiazolyl, benzotriazolyl, or carbazolyl, and preferably monocyclic heteroaryl, more preferably pyridyl, furyl, thienyl, oxazolyl, isoxazolyl, oxadiazolyl, thiazolyl, isothiazolyl, or thiadiazolyl.

The expression "which may be substituted" means "unsubstituted" or "having 1 to 5 substituents which may be the same as or different from one another". The term "substituted" means "having 1 to 5 substituents which may be the same as or different from one another". In addition, in a case where a plurality of substituents is present, the substituents may be the same as or different from one another.

The substituent in the "aryl" and the "heterocyclic group", each of which may be substituted, in $R^{1a}$ is preferably a group selected from the following Group $G^1$ (in which $R^O$ means —H or lower alkyl; and the same shall apply hereinafter), and more preferably halogen, lower alkyl, halogeno-lower alkyl, —O-lower alkyl, —O-halogeno-lower alkyl, —C(O)NH$_2$ or heteroaryl, and still more preferably halogen, halogeno-lower alkyl, or —C(O)NH$_2$.

Group $G^1$: halogen, cyano, lower alkyl, halogeno-lower alkyl, lower alkylene-OR$^O$, lower alkylene-N(R$^O$)$_2$, lower alkylene-N(R$^O$)C(O)R$^O$, lower alkylene-N(R$^O$)S(O)$_2$-lower alkyl, —OR$^O$, —O-halogeno-lower alkyl, —O-cycloalkyl, —O-aryl, —O-heterocyclic group, —C(O)R$^O$, —CO$_2$R$^O$, —C(O)NH$_2$, —C(O)N(R$^O$)-(lower alkyl which may be substituted with —OR$^O$ or —CO$_2$R$^O$), —C(O)N(R$^O$)-lower alkylene-OR$^O$, —C(O)N(R$^O$)-lower)alkylene-N(R$^O$)$_2$, —C(O)N(R$^O$)-lower alkylene-S-lower alkyl, —C(O)N(R$^O$)-lower alkylene-S(O)-lower alkyl, —C(O)N(R$^O$)-lower alkylene-S(O)$_2$-lower alkyl, —C(O)N(R$^O$)-lower alkylene-C(O)N(R$^O$)$_2$, —C(O)N(R$^O$)-lower alkylene-C(O)N(R$^O$)-cycloalkyl, —C(O)N(R$^O$)-lower alkylene-heterocyclic group, —C(O)N(R$^O$)-cycloalkyl, —C(O)N(R$^O$)-heterocyclic group, —C(O)N(R$^O$)N(R$^O$)$_2$, —C(O)N(R$^O$)N(R$^O$)C(O)R$^O$, —C(O)N(R$^O$)S(O)$_2$-lower alkyl, —C(O)-heterocyclic group, —C(=NOR$^O$)—N(R$^O$)$_2$, —S-lower alkyl, —S(O)-lower alkyl, —S(O)$_2$-lower alkyl, oxo, and a heterocyclic group.

In this case, the aryl and the heterocyclic group in Group $G^1$ may be substituted with a group selected from the following Group $G^2$.

Group $G^2$: halogen, cyano, lower alkyl, halogeno-lower alkyl, —OR$^O$, —O-halogeno-lower alkyl, —CO$_2$R$^O$, —C(O)N(R$^O$)$_2$, —C(O)N(R$^O$)S(O)$_2$-lower alkyl, —C(O)N(R$^O$)S(O)$_2$N(R$^O$)$_2$, cycloalkyl, and a heterocyclic group.

The substituent in the "aryl", "heterocyclic group", and "cycloalkyl", each of which may be substituted, in Ring A is preferably a group selected from the following Group $G^3$, more preferably halogen, lower alkyl, halogeno-lower alkyl, —O-lower alkyl, —O-halogeno-lower alkyl, or —C(O)NH$_2$, and still more preferably halogen, halogeno-lower alkyl, or —C(O)NH$_2$.

Group G$^3$: halogen, cyano, lower alkyl, halogeno-lower alkyl, lower alkylene-OR$^0$, halogeno-lower alkylene-OR$^0$, lower alkylene-N(R$^0$)$_2$, lower alkylene-aryl, —OR$^0$, —O-halogeno-lower alkyl, —O-lower alkylene-OR$^0$, —O-lower alkylene-N(R$^0$)$_2$, —O-lower alkylene-CO$_2$R$^0$, —O-lower alkylene-C(O)N(R$^0$)$_2$, —O-lower alkylene-aryl, —O-aryl, —C(O)R$^0$, —CO$_2$R$^0$, —CON(R$^0$)$_2$, —CON(R$^0$)-lower alkylene-OR$^0$, —N(R$^0$)$_2$, —N(R$^0$)C(O)R$^0$, —S-lower alkyl, —S(O)-lower alkyl, —S(O)$_2$-lower alkyl, —S(O)$_2$-aryl, oxo, cycloalkyl, aryl, and a heterocyclic group.

In this case, the aryl and heterocyclic group in Group G$^3$ may be substituted with halogen, lower alkyl, halogeno-lower alkyl, —OR$^0$, —O-halogeno-lower alkyl, —CO$_2$R$^0$, or —CON(R$^0$)$_2$.

The substituent in the "aryl" which may be substituted in R$^{1b}$ is preferably halogen, lower alkyl, halogeno-lower alkyl, —O-lower alkyl, or —O-halogeno-lower alkyl, and more preferably halogen.

The substituent in the "aryl" and the "heteroaryl", each of which may be substituted, in Ring A$^b$ is preferably halogen, lower alkyl, halogeno-lower alkyl, —O-lower alkyl, —O-halogeno-lower alkyl or —C(O)NH$_2$, and still more preferably halogen, halogeno-lower alkyl, or —C(O)NH$_2$.

The "11β-HSD1 inhibitor" is a compound inhibiting the enzyme activity of an 11β-HSD1, and not particularly limited as long as it is effective for pains. Preferably, the 11β-HSD1 inhibitor is a compound having an IC$_{50}$ value of 10 μM or less, more preferably 3 μM or less, and still more preferably 1 μM or less in the measurement test on the rat 11β-HSD1 inhibitory activity according to the test method described in Example 1 described later.

The "pain" is preferably neuropathic pain. Further, in other embodiments, it is preferably fibromyalgia.

Preferred embodiments of the compound represented by the formula (I-a), which is an active ingredient for the pharmaceutical of the present invention, are shown below.

(1) A compound represented by the formula (I-b):

[Chem. 13]

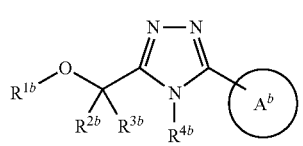

(I-b)

[the symbols in the formula denote the following meanings:

R$^{1b}$: aryl which may be substituted,

R$^{2b}$: lower alkyl,

R$^{3b}$: lower alkyl,

R$^{4b}$: lower alkyl or cycloalkyl,

Ring A$^b$: aryl or heteroaryl, each of which may be substituted, and the other symbols have the same meanings].

(2) A compound represented by the formula (I-c):

[Chem. 14]

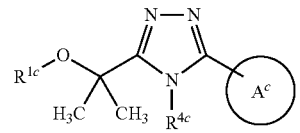

(I-c)

[the symbols in the formula denote the following meanings:

R$^{1c}$: phenyl substituted with halogen,

R$^{4c}$: methyl, ethyl, isopropyl, or cyclopropyl, and

Ring A$^c$: phenyl substituted with halogen or —C(O)NH$_2$].

(3) The compound as set forth in (2), wherein Ring A$^c$ is phenyl, which is substituted with —C(O)NH$_2$ at the 4-position and may be further substituted with halogen.

(4) The compound as set forth in (2), wherein Ring A$^c$ is phenyl substituted with halogen.

(5) A compound selected from the group consisting of:
3-(2-bromo-4-fluorophenyl)-4-methyl-5-[1-methyl-1-(2,4,6-trifluorophenoxy)ethyl]-4H-1,2,4-triazole,
3-(2-chloro-4-fluorophenyl)-4-methyl-5-[1-methyl-1-(2,4,6-trifluorophenoxy)ethyl]-4H-1,2,4-triazole,
3-(2-chlorophenyl)-4-methyl-5-[1-methyl-1-(2,4,6-trifluorophenoxy)ethyl]-4H-1,2,4-triazole,
3-[1-(4-chloro-2,6-difluorophenoxy)-1-methylethyl]-5-(2-chlorophenyl)-4-methyl-4H-1,2,4-triazole,
3-[1-(4-chloro-2,6-difluorophenoxy)-1-methylethyl]-5-(2-chloro-4-fluorophenyl)-4-methyl-4H-1,2,4-triazole,
3-(2-fluorophenyl)-4-methyl-5-[1-methyl-1-(2,4,6-trifluorophenoxy)ethyl]-4H-1,2,4-triazole,
4-methyl-3-[1-methyl-1-(2,4,6-trifluorophenoxy)ethyl]-5-[3-(trifluoromethyl)-1H-pyrazol-4-yl]-4H-1,2,4-triazole,
4-{5-[1-(4-chloro-2,6-difluorophenoxy)-1-methylethyl]-4-ethyl-4H-1,2,4-triazol-3-yl}benzamide,
4-{4-isopropyl-5-[1-methyl-1-(2,4,6-trifluorophenoxy)ethyl]-4H-1,2,4-triazol-3-yl}benzamide,
4-{5-[1-(4-chloro-2,6-difluorophenoxy)-1-methylethyl]-4-methyl-4H-1,2,4-triazol-3-yl}-3-fluorobenzamide,
4-{4-cyclopropyl-5-[1-(2,4-difluorophenoxy)-1-methylethyl]-4H-1,2,4-triazol-3-yl}-3-fluorobenzamide,
3-fluoro-4-{4-methyl-5-[1-methyl-1-(2,4,6-trifluorophenoxy)ethyl]-4H-1,2,4-triazol-3-yl}benzamide,
4-{5-[1-(4-chloro-2,6-difluorophenoxy)-1-methylethyl]-4-isopropyl-4H-1,2,4-triazol-3-yl}benzamide,
3-chloro-4-{4-cyclopropyl-5-[1-methyl-1-(2,4,6-trifluorophenoxy)ethyl]-4H-1,2,4-triazol-3-yl}benzamide, and
3-fluoro-4-{4-isopropyl-5-[1-methyl-1-(2,4,6-trifluorophenoxy)ethyl]-4H-1,2,4-triazol-3-yl}benzamide.

Other preferred embodiments of the compound of the formula (I-a) which is an active ingredient for the pharmaceutical of the present invention are shown below.

(a) R$^{1a}$ is preferably aryl which may be substituted, more preferably phenyl which may be substituted, still more preferably phenyl substituted with halogen, and even still more preferably phenyl substituted with halogens at the 2- and 4-positions, or phenyl substituted with halogens at the 2-, 4-, and 6-positions.

(b) R$^{2a}$ is preferably lower alkyl, and more preferably methyl.

(c) R$^{3a}$ is preferably lower alkyl, and more preferably methyl.

(d) R⁴ is preferably lower alkyl or cycloalkyl, and more preferably methyl, ethyl, isopropyl, or cyclopropyl.

(e) Ring A is preferably aryl or heteroaryl, each of which may be substituted, more preferably aryl which may be substituted, still more preferably phenyl which may be substituted, even still more preferably phenyl substituted with halogen or —C(O)NH₂, even still more preferably phenyl substituted with halogen, particularly preferably phenyl substituted with halogen at the 2-position, or phenyl substituted with halogens at the 2- and 4-positions. In another embodiment, Ring A is preferably phenyl which is substituted with —C(O)NH₂ and may be further substituted with halogen, more preferably phenyl which is substituted with —C(O)NH₂ at the 4-position and may be further substituted with halogen. Further, in a further embodiment, Ring A is preferably phenyl or pyrrole, each of which is substituted with a group selected from halogen, halogeno-lower alkyl, and —C(O)NH₂.

(f) The compound formed by two or more combination of the groups described in (a) to (e) above.

The compound of the formula (I-a) which is an active ingredient for the pharmaceutical of the present invention may exist in the form of tautomers or geometrical isomers depending on the kind of substituents. In the present specification, the compound of the formula (I-a) shall be described in only one form of isomer, but the active ingredient for the pharmaceutical of the present invention includes other isomers, isolated forms of the isomers, or a mixture thereof.

In addition, the compound of the formula (I-a) which is an active ingredient for the pharmaceutical of the present invention may have asymmetric carbon atoms or axial chirality in some cases, and correspondingly, it may exist in the form of optical isomers. The active ingredient for the pharmaceutical of the present invention includes both an isolated form of the optical isomers or a mixture thereof.

Furthermore, the compound of the formula (I-a) which is an active ingredient for the pharmaceutical of the present invention also includes a pharmaceutically acceptable prodrug thereof. The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and "Iyakuhin no Kaihatsu (Pharmaceutical Research and Development)" (Hirokawa Publishing Company, 1990), Vol. 7, Bunshi Sekkei (Molecular Design), 163-198.

Moreover, the compound of the formula (I-a) which is an active ingredient for the pharmaceutical of the present invention may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like, or organic bases such as methylamine, ethylamine, ethanolamine, lysine, ornithine, and the like, salts with various amino acids or amino acid derivatives such as acetylleucine and the like, ammonium salts, etc.

Moreover, the compound of the formula (I-a) which is an active ingredient for the pharmaceutical of the present invention also includes various hydrates or solvates, and crystal polymorphs. In addition, the compound of the formula (I-a) which is an active ingredient for the pharmaceutical of the present invention also includes compounds labeled with various radioactive or non-radioactive isotopes.

(Preparation Methods)

The compound of the formula (I-a) and a salt thereof, which are active ingredients for the pharmaceutical of the present invention, can be prepared using the characteristics based on the basic structure or the type of substituent and by applying various known synthesis methods. During the preparation, replacement of the relevant functional group with a suitable protective group (a group that can be easily converted into the relevant functional group) at the stage from starting material to an intermediate may be effective depending on the type of the functional group in the production technology in some cases. The protective group for such a functional group may include, for example, the protective groups described in "Greene's Protective Groups in Organic Synthesis (4ᵗʰ Ed, 2006)" written by P. G. M. Wuts and T. W. Greene, and one of these should only be selected and used as necessary depending on reaction conditions. In such a method, a desired compound can be obtained by introducing the protective group, by carrying out a reaction and by eliminating the protective group as necessary.

In addition, the prodrug of the compound of the formula (I-a) can be produced by introducing a specific group at the stage from a starting material to an intermediate or by carrying out the reaction using the obtained compound of the formula (I-a), just as in the case of the above-mentioned protective group. The reaction can be carried out using methods known to those skilled in the art, such as ordinary esterification, amidation, dehydration, and the like.

Hereinbelow, typical preparation methods for the compound of the formula (I-a) will be described. Each of the production processes may also be carried out with reference to the References appended in the present description. Further, the preparation methods of the present invention are not limited to the examples shown below.

(Preparation Process 1)

[Chem. 15]

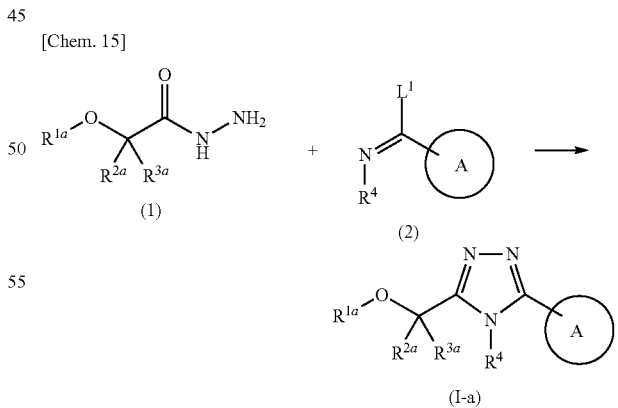

(In the formula, L¹ represents a leaving group. The same shall apply hereinafter.)

The present production process is a method for preparing the compound (I-a) which is an active ingredient for the pharmaceutical of the present invention by cyclization of a compound (1) with a compound (2). Examples of the leaving group of $L^1$ include chloro, bromo, methoxy, methylsulfanyl, and the like. The reaction can be carried out in a solvent, for example, such as ethers such as tetrahydrofuran (THF), 1,4-dioxane, diglyme, and the like; alcohols such as methanol, ethanol, propanol, butanol, and the like; aprotic polar solvents such as N,N-dimethylformamide (DMF), N-methylpyrrolidin-2-one (NMP), dimethylimidazolidinone, dimethylacetamide (DMA), dimethylsulfoxide (DMSO), and the like; aromatic hydrocarbons such as benzene, toluene, xylene, and the like; halogenated hydrocarbons such as dichloromethane, chloroform, 1,2-dichloroethane, and the like; etc., at room temperature or under heating conditions. Depending on the compound, it may be advantageous in some cases to carry out the reaction in the presence of an acid, for example, an organic acid such as acetic acid, p-toluenesulfonic acid, and the like; a mineral acid such as sulfuric acid, hydrochloric acid, and the like; etc., or in the presence of an organic base such as triethylamine, N,N-diisopropylethylamine, and the like; or an inorganic base such as sodium hydrogen carbonate, potassium carbonate, and the like. Depending on the compound, it may be advantageous in some cases to carry out the reaction in the presence of a phase transfer catalyst such as tetra-n-butylammonium iodide and the like.

(Preparation Process 2)

[Chem. 16]

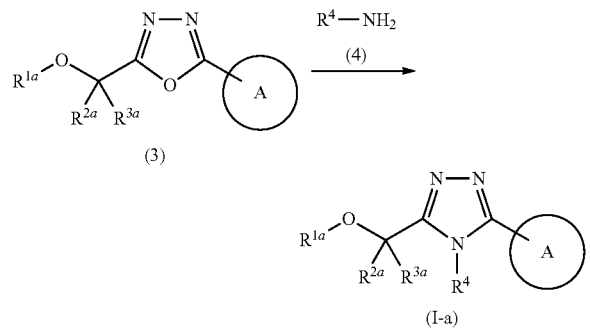

(I-a)

The present preparation process is a method for obtaining the compound (I-a) which is an active ingredient for the pharmaceutical of the present invention by reacting a compound (3) with a compound (4).

The reaction can be carried out using the compound (3) and the compound (4) in equivalent amounts, or with either thereof in an excess amount in a solvent inert to the reaction, for example, alcohols, aromatic hydrocarbons such as benzene, toluene, xylene, and the like, acetic acid, or the like, or in the absence of a solvent, under room temperature to heating, preferably under heating. Depending on the compound, it may be advantageous in some cases to carry out the reaction in the presence of an acid, for example, an organic acid such as acetic acid, p-toluenesulfonic acid, trifluoroacetic acid, and the like; a mineral acid such as sulfuric acid, hydrochloric acid, and the like; etc. Also, it is advantageous in some cases to carry out the reaction using a microwave.

(Preparation Process 3)

[Chem. 17]

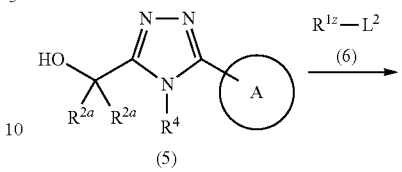

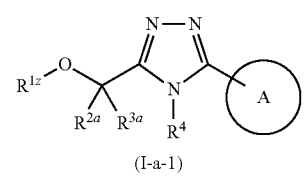

(I-a-1)

(In the formula, $R^{1z}$ is aryl or heteroaryl, each of which may be substituted, and $L^2$ represents a leaving group. The same shall apply hereinafter.)

The present preparation process is a method for obtaining the compound (I-a-1) which is an active ingredient for the pharmaceutical of the present invention, by O-arylation of a compound (5). Examples of the leaving group of $L^2$ include halogen such as fluoro, chloro, bromo and the like.

The arylation reaction can be carried out using a compound (5) and a compound (6) in equivalent amounts, or with either thereof in an excess amount, under cooling to heating with refluxing, in the presence of a base, in a solvent inert to the reaction, such as an aprotic polar solvent such as DMF, DMSO, and the like; ethers; etc. Examples of the base include sodium hydride, potassium hydride, butyl lithium, potassium carbonate and the like.

(Preparation Process 4)

[Chem. 18]

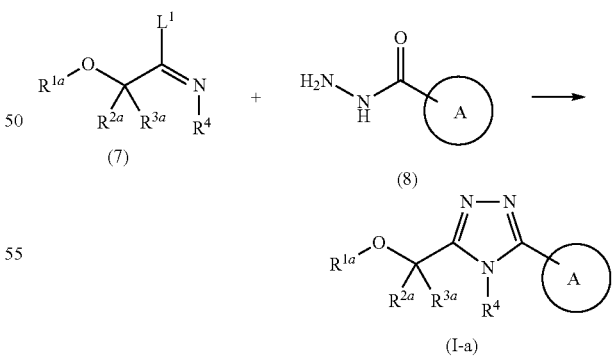

(I-a)

The present preparation process is a method for preparing the compound (I-a) which is an active ingredient for the pharmaceutical of the present invention by cyclization reaction of a compound (7) with a compound (8).

The cyclization reaction can be carried out in the same manner as in the Production Process 1.

(Preparation Process 5)

[Chem. 19]

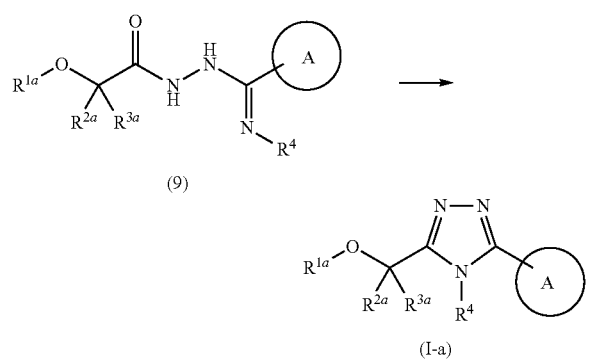

The present preparation process is a method for obtaining the compound (I-a) which is an active ingredient for the pharmaceutical of the present invention by cyclization of a compound (9).

The cyclization reaction can be carried out in a solvent such as ethers, aromatic hydrocarbons, halogenated hydrocarbons, and the like, at room temperature or under heating conditions. Depending on the compound, it may be advantageous in some cases for the progress of the reaction that the reaction is carried out in the presence of an acid such as an organic acid such as acetic acid, p-toluenesulfonic acid, and the like, or a mineral acid such as sulfuric acid, hydrochloric acid, and the like, etc.

Furthermore, several compounds represented by the formula (I-a) can also be prepared from the compound (I-a) which is an active ingredient for the pharmaceutical of the present invention obtained as above by optionally combining processes commonly adoptable by those skilled in the art, such as known alkylation, acylation, substitution reaction, oxidation, reduction, hydrolysis, and the like.

The starting materials for use in the preparation of the compound (I-a) which is an active ingredient for the pharmaceutical of the present invention can be prepared by applying the methods described below, the methods described in Preparation Examples to be mentioned below, known methods or methods obvious to those skilled in the art, or modified methods thereof.

(Starting Material Synthesis 1)

[Chem. 20]

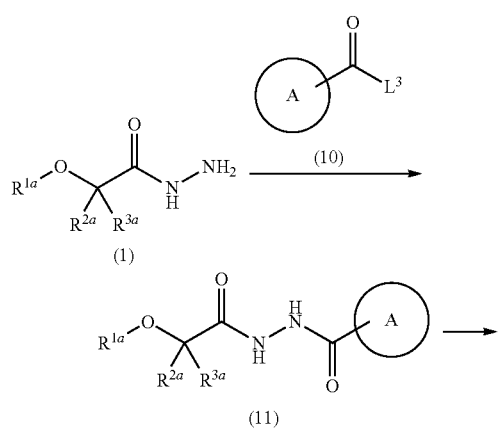

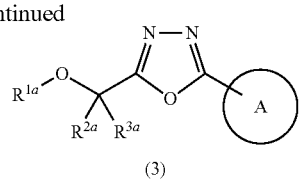

(In the formula, $L^3$ represents a leaving group. The same shall apply hereinafter.)

The compound (3) can be prepared by cyclization of compound (11) obtained by amidation of the compound (1) and a compound (10). Here, examples of the leaving group of $L^3$ include chloro, bromo, hydroxy, and the like.

The amidation reaction can be carried out using the compound (1) and the compound (10) in equivalent amounts, or with either thereof in an excess amount, in a solvent such as halogenated hydrocarbons, aprotic polar solvents, and the like, under room temperature to heating conditions. Depending on the compounds, it is advantageous for the smooth progress of the reaction in some cases to carry out the reaction in the presence of an organic base such as triethylamine, N,N-diisopropylethylamine, pyridine, and the like, or an inorganic base such as potassium carbonate, sodium carbonate, and the like.

In the case where the leaving group of $L^3$ is hydroxy, it is preferable that the reaction be carried out in the presence of a condensing agent such as 1-(3-dimethylaminopropyl)-3-ethylcarbodiimide (WSC), dicyclohexylcarbodiimide (DCC), 1,1'-carbonyldiimidazole (CDI), O-(benzotriazol-1-yl)-N,N,N',N'-tetramethyluroniumhexafluorophosphate (HBTU), and the like. In addition, it is preferable in some cases that an additive (for example, 1-hydroxybenzotriazole (HOBt), 1-hydroxy-7-azabenzotriazole (HOAt), and the like) is used.

The cyclization reaction can be carried out by reacting the compound (11) with a dehydrating agent such as phosphorus oxychloride, trifluoromethanesulfonic anhydride, a reagent prepared from triphenylphosphine and carbon tetrabromide, and the like in a solvent such as an aprotic polar solvent such as halogenated hydrocarbons and the like. Depending on the compound, it is advantageous for the smooth progress of the reaction in some cases to carry out the reaction in the presence of an organic base such as triethylamine, N,N-diisopropylethylamine, pyridine, and the like, or an inorganic base such as potassium carbonate, sodium carbonate, and the like.

(Starting Material Synthesis 2)

[Chem. 21]

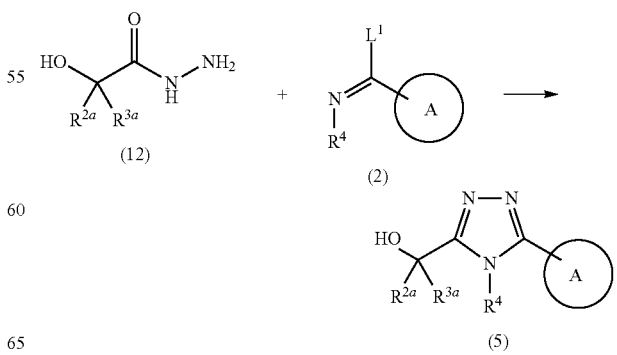

The compound (5) can be prepared from a compound (12) and the compound (2) in the same manner as in the Preparation Process 1.

(Starting Material Synthesis 3)

[Chem. 22]

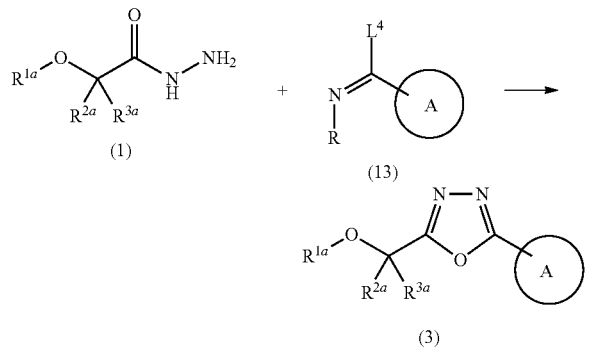

(In the formula, R represents lower alkyl and $L^4$ represents a leaving group. The same shall apply hereinafter.)

In addition, the compound (3) can also be prepared by cyclization of the compound (1) with a compound (13). Here, examples of the leaving group of $L^4$ include chloro, bromo, and the like.

The reaction can be carried out in the same manner as in the Preparation Process 1.

(Starting Material Synthesis 4)

[Chem. 23]

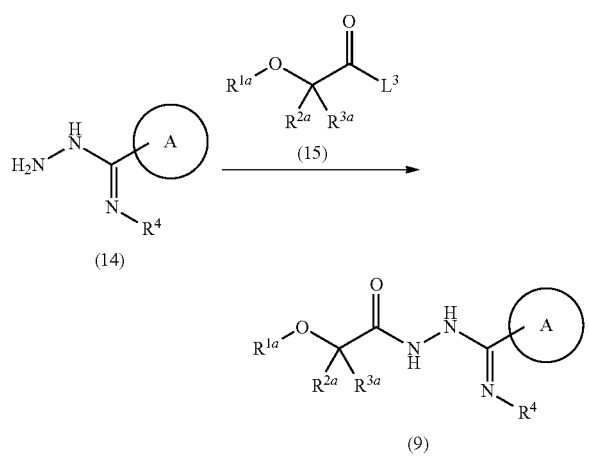

The compound (9) can be prepared by the amidation reaction of a compound (14) and a compound (15).

The amidation reaction can be carried out in the same condition as in the amidation of the first step of the starting material synthesis 1.

The compound of the formula (I-a) is isolated and purified as a free compound or a salt, a hydrate, a solvate, or a crystal polymorph thereof. The salt of the compound of the formula (I-a) can also be prepared using a conventional salt formation reaction.

Isolation and purification are carried out by applying common chemical operations such as extraction, fractional crystallization, various types of fractional chromatography, and the like.

A variety of isomers can be prepared by selecting suitable starting compounds or separated using differences in the physicochemical properties between the isomers. For example, optical isomers are obtained by a general optical resolution method of racemic forms (for example, fractional crystallization in which the racemic form is converted into diastereomer salts with an optically active base or acid, chromatography using a chiral column and the like, and the like), or can also be prepared from suitable starting compounds which are optically active.

A pharmaceutical composition for treating pain of the present invention, including one or two or more kinds of the compound of the formula (I-a) as an active ingredient, can be prepared using excipients that are usually used in the art, that is, excipients for pharmaceutical preparation, carriers for pharmaceutical preparation, and the like, according to the methods usually used.

Administration can be accomplished either by oral administration via tablets, pills, capsules, granules, powders, solutions, and the like, or parenteral administration via injections, such as intraarticular, intravenous, or intramuscular injections, and the like, suppositories, eye drops, eye ointments, transdermal liquid preparations, ointments, transdermal patches, transmucosal liquid preparations, transmucosal patches, inhalers, and the like.

As a solid composition for oral administration, tablets, powders, granules, and the like are used. In such a solid composition, one or two or more kinds of the active ingredient(s) are mixed with at least one inactive excipient. In a conventional method, the composition may contain inactive additives, such as a lubricant, a disintegrating agent, a stabilizer, or a solubilization assisting agent. If necessary, tablets or pills may be coated with sugar or with a film of a gastric or enteric coating substance.

The liquid composition for oral administration includes pharmaceutically acceptable emulsions, solutions, suspensions, syrups, elixirs, or the like, and also includes generally used inert diluents, for example, purified water or ethanol. In addition to the inert diluent, the liquid composition may also include auxiliary agents such as a solubilization assisting agent, a moistening agent, and a suspending agent, sweeteners, flavors, aromatics, and antiseptics.

The injections for parenteral administration include sterile aqueous or non-aqueous solution preparations, suspensions, or emulsions. The aqueous solvent includes, for example, distilled water for injection and physiological saline. Examples of the non-aqueous solvent include alcohols such as ethanol. Such a composition may further include a tonicity agent, an antiseptic, a moistening agent, an emulsifying agent, a dispersing agent, a stabilizing agent, or a solubilizing assisting agent. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

The agent for external use includes ointments, plasters, creams, jellies, patches, sprays, lotions, eye drops, eye ointments, and the like. The agents include generally used ointment bases, lotion bases, aqueous or non-aqueous liquid preparations, suspensions, emulsions, and the like.

The transmucosal agents such as an inhaler, a transnasal agent, and the like, those in the form of a solid, liquid, or semi-solid state are used, can be prepared in accordance with a conventionally known method. For example, a known excipient, and also a pH adjusting agent, an antiseptic, a surfactant, a lubricant, a stabilizing agent, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device such as a measured administration inhalation device, and the like, or sprayer. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, carbon dioxide, and the like, or other forms.

Usually, in the case of oral administration, the daily dose is from about 0.001 to 100 mg/kg, preferably from 0.1 to 30 mg/kg, and more preferably from 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once or plural times a day. The dose is appropriately decided in response to the individual case by taking the symptoms, the age, and the gender, and the like into consideration.

A therapeutic agent for pain including the compound of the formula (I-a) or a pharmaceutically acceptable salt thereof as an active ingredient may be used in combination with other therapeutic agents for pain. Such the combined preparations may be administered simultaneously, or separately and continuously, or at a desired time interval. The preparations to be co-administered may be a blend, or may be prepared individually.

EXAMPLES

Hereinafter, the present invention will be described in detail with reference to Examples, but these do not restrict the scope of the present invention.

Example 1

Measurement Test for Rat 11β-HSD1 Inhibitory Activity

The procedure for measuring the 11β-HSD1-inhibitory activity is as follows. The enzyme reaction and the measurement were carried out using a 384-well plate. The enzyme was prepared in accordance with Journal of Biological Chemistry, 2001, Vol. 276, p. 21343-21350. The reaction was carried out by adding a test compound at various concentrations to a reaction liquid consisting of a 5 mM phosphate buffer (pH 6.6), 200 nM cortisone, 40 μM reduced nicotinamide adenine dinucleotide phosphate (NADPH), and rat recombinant 11β-HSD1, followed by incubating at room temperature for one hour (10 μl/well). The test compound was prepared by dissolving in dimethyl sulfoxide (DMSO) such that a DMSO concentration reached 1% in the reaction liquid. After the enzyme reaction was completed, the enzyme inhibitory action was measured by detecting cortisol using a homogeneous time-resolved fluorescence (HTRF) method. Each of a d2-labeled cortisol containing 400 μM carbenoxolone and a cryptate-labeled cortisol antibody (CIS Bio International Co., Ltd.) was added at 5 μl/well, followed by incubating at room temperature for 2 hours, and then the fluorescence intensity was measured using a fluorophotometer (trade name: ARVO HTS 1420, Perkin Elmer/Wallac), and the enzyme inhibitory activity was calculated from the fluorescence intensity ratio of two wavelengths (665 nm/620 nm).

The measurement results were calculated by averaging the values of 3 wells of the same condition. The ratio when DMSO was added instead of the test compound was taken as 0% and the ratio when 11β-HSD1 was not added was taken as 100%, thereby calculating the 50% inhibition concentration of the test compound as $IC_{50}$ of the compound inhibitory activity.

The $IC_{50}$ values of the typical compounds with respect to the active ingredients for the pharmaceutical of the present invention are shown in Table 1 below. Further, Cpd represents Compound No. (the same shall apply hereinafter).

TABLE 1

| Cpd | $IC_{50}$ (nM) |
|---|---|
| 1 | 35 |
| 2 | 52 |
| 3 | 24 |
| 4 | 32 |
| 5 | 263 |
| 6 | 322 |
| 7 | 32 |
| 8 | 70 |
| 9 | 26 |
| 10 | 135 |
| 11 | 64 |
| 12 | 182 |
| 13 | 68 |
| 14 | 16 |
| 15 | 23 |

Example 2

Test of Spinal Nerve Ligation Model

The test was carried out in accordance with Pain, 1992, Vol. 50, p. 355-363. The lumbar skin and muscle of a rat (SD, male, 5- to 6-week old) were incised under pentobarbital anesthesia and the transverse processes of lumbar L6 were removed to expose lumbar nerves. The L5 and L6 spinal nerves were ligated with silk thread and then the wound was sutured. The treatment was performed on the left side. However, in a case of a pseudo-operation, the wound was sutured without carrying out the nerve ligation.

Drug efficacy evaluation was carried out by a von Frey hair test 7 to 20 days after the operation. The withdrawal response threshold was calculated in accordance with Journal of Neuroscience Methods, 1994, Vol. 53, p. 55-63. The plantar of hindlimb was stimulated using 8 kinds of von Frey filaments (0.41 to 15.14 g), and 50% withdrawal response thresholds were determined by an up-and-down method. The test was initiated from 2.04 g of the filament, and a case where the withdrawal response of the limb was observed was taken as presence of the response.

On the previous day of the drug efficacy evaluation, the animals showing reduction in the thresholds according to a von Frey hair test were preliminarily selected and grouped such that the difference in the average values of the thresholds between the respective groups was reduced.

The test substance was suspended in a 0.5% methylcellulose solution and administered orally 2 hours before the drug efficacy evaluation. The evaluation of the test substance was carried out by determining the improvement rate of the group administered with the test substance when the threshold of the limb on the treatment side in the pseudo-operation animal group was taken as 100% and the threshold of the limb on the treatment side in an operated animal group administered with a solvent was taken as 0%.

The improvement rates of the typical compounds with respect to the active ingredients for the pharmaceuticals of the present invention are shown in Table 2 below.

TABLE 2

| Cpd | Improvement rate % (dose) |
|---|---|
| 1 | 71 (0.3 mg/kg) |
| 2 | 88 (0.3 mg/kg) |
| 3 | 62 (0.3 mg/kg) |
| 4 | 85 (0.3 mg/kg) |
| 5 | 65 (0.3 mg/kg) |
| 6 | 52 (0.3 mg/kg) |
| 7 | 73 (0.3 mg/kg) |
| 8 | 87 (0.3 mg/kg) |
| 9 | 78 (0.3 mg/kg) |
| 10 | 81 (0.3 mg/kg) |
| 11 | 82 (0.3 mg/kg) |
| 12 | 54 (0.3 mg/kg) |
| 13 | 53 (0.3 mg/kg) |
| 14 | 73 (0.3 mg/kg) |
| 15 | 86 (0.3 mg/kg) |

Example 3

Test of Fibromyalgia Model Induced by Repeated Administration of Reserpine

The test was carried out in accordance with Pain, 2009, Vol. 146, p. 26-33. Rats (SD, male, 7 weeks old) were used.

The threshold measurement for the muscle pressure pain was carried out according to the method of Schafers et al. (Pain, 2003, Vol. 104, p. 579-588). The pressure stimulus gradually increasing up to 250 g was applied to the gastrocnemius muscle of the right hindlimb of the rat. The magnitude of the minimum pressure stimulus at which the rat showed a withdrawal response with respect to pressure stimulus of the right hindlimb was measured as a muscle pressure pain threshold (g). The measurements were carried out in triplicate for each point of time and the average thereof was taken as a measured value.

A solvent (0.5% acetic acid/water) or reserpine at 1 mg/kg was subcutaneously administered on a dorsal subcutaneous part for 3 days once per day. The administration volume of the solvent or reserpine was taken as 1 mL per kg of a body weight of an animal. The muscle pressure pain thresholds of the respective rats were measured at 6 days after the initiation of the administration of the solvent or reserpine, and grouped such that the difference in the average values of the thresholds between the respective groups was reduced.

The drug efficacy evaluation was carried out the next day. The test substance was suspended in a 0.5% methylcellulose solution and the muscle pressure pain thresholds were measured 30, 60, and 120 minutes after oral administration. For the normal rats, drug administration was not carried out, and only the measurement of the muscle pressure pain thresholds was carried out. The measurement of the drug effect was carried out by an experimenter who does not know the drug treatment context to an animal. The evaluation of the test substance was carried out by determining the maximal improvement rate of the group administered with the test substance among at time points of 30, 60, and 120 minutes after the administration when the muscle pressure pain threshold of the normal rat is taken as 100% and the muscle pressure pain threshold of the rat treated with reserpine while administered with the solvent is taken as 0%.

The improvement rates of the typical compounds with respect to the active ingredients for the pharmaceuticals of the present invention are shown in Table 3 below.

TABLE 3

| Cpd | Maximum improvement rate % (dose) | Point for calculation (min) |
|---|---|---|
| 2 | 30 (1 mg/kg) | 120 |
| 4 | 82 (1 mg/kg) | 30 |
| 8 | 41 (1 mg/kg) | 120 |
| 10 | 65 (1 mg/kg) | 120 |
| 11 | 83 (1 mg/kg) | 30 |
| 15 | 45 (1 mg/kg) | 120 |

As the results of the tests above, it was confirmed that the compound represented by the formula (I-a) is effective in various pain models. Therefore, it is apparent that the compound represented by the formula (I-a) which is an active ingredient for the pharmaceutical of the present invention can be used for the treatment of pain (in particular, neuropathic pain, fibromyalgia, or the like).

The methods for preparing the compounds with respect to the active ingredients for the pharmaceuticals of the present invention are shown below.

All the compounds 1 to 15 described in Tables 4 to 6 below are known compounds and can be prepared in the following manner.

All the compounds 1 to 15 are described as Example compounds in the pamphlet of International Publication WO 2010/001946, and can be prepared by the method described in this publication. For example, the compound 2 is described as Example 65 of this publication.

The following abbreviations are used in Tables below.

Cpd: Compound No., Structure: Structural formula (in the case where HCl is described in the structural formula, it denotes that the compound is hydrochloride salt).

TABLE 4

| Cpd | Structure |
|---|---|
| 1 | [Structural formula of compound 1 with HCl] |
| 2 | [Structural formula of compound 2 with HCl] |
| 3 | [Structural formula of compound 3 with HCl] |

TABLE 4-continued

| Cpd | Structure |
|---|---|
| 4 | 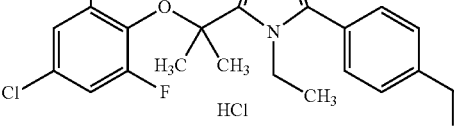 |
| 5 | 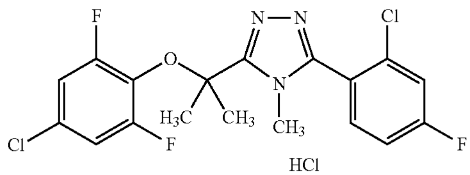 [SMILES: Cn1c(-c2ccc(F)cc2Cl)nnc1C(C)(C)Oc1c(F)cc(Cl)cc1F ; Cl] |
| 6 | 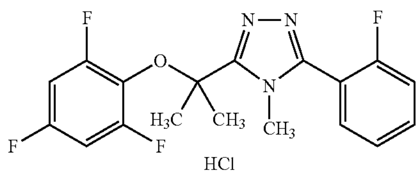 [SMILES: Cn1c(-c2ccccc2F)nnc1C(C)(C)Oc1c(F)cc(F)cc1F ; Cl] |
| 7 | 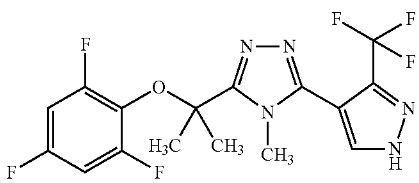 [SMILES: Cn1c(-c2c[nH]nc2C(F)(F)F)nnc1C(C)(C)Oc1c(F)cc(F)cc1F] |

TABLE 5

| 8 | |
| --- | --- |
| 9 | |
| 10 | |
| 11 | 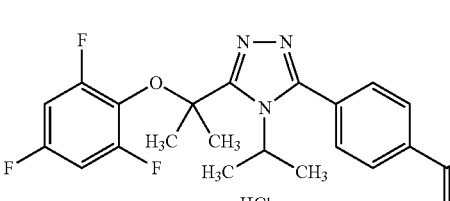 |
| 12 | |
| 13 | |
| 14 | |

TABLE 6

| 15 | 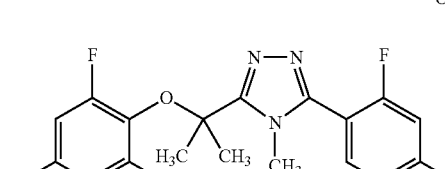 |
| --- | --- |

INDUSTRIAL APPLICABILITY

An 11β-HSD1 inhibitor which is an active ingredient for the pharmaceutical of the present invention, in particular, the compound of the formula (I-a), is useful for the treatment of pain (in particular, neuropathic pain or fibromyalgia).

The invention claimed is:

1. A method for treating neuropathic pain, comprising administering, to a subject in need thereof, an effective amount of a compound selected from the group consisting of:
   3-(2-chloro-4-fluorophenyl)-4-methyl-5-[1-methyl-1-(2,4,6-trifluorophenoxy)ethyl]-4H-1,2,4-triazole,
   3-[1-(4-chloro-2,6-difluorophenoxy)-1-methylethyl]-5-(2-chlorophenyl)-4-methyl-4H-1,2,4-triazole,
   4-{5-[1-(4-chloro-2,6-difluorophenoxy)-1-methylethyl]-4-ethyl-4H-1,2,4-triazol-3-yl}benzamide,
   4-{5-[1-(4-chloro-2,6-difluorophenoxy)-1-methylethyl]-4-methyl-4H-1,2,4-triazol-3-yl}-3-fluorobenzamide, 4-{4-cyclopropyl-5-[1-(2,4-difluorophenoxy)-1-methylethyl]-4H-1,2,4-triazol-3-yl}-3-fluorobenzamide, and 3-fluoro-4-{4-isopropyl-5-[1-methyl-1-(2,4,6-trifluorophenoxy)ethyl]-4H-1,2,4-triazol-3-yl}benzamide, or a pharmaceutically acceptable salt thereof, wherein said compound is administered at a daily dose of 0.001 to 100 mg/kg body weight.

2. The method according to claim 1, wherein said compound is 3-[1-(4-chloro-2,6-difluorophenoxy)-1-methylethyl]-5-(2-chlorophenyl)-4-methyl-4H-1,2,4-triazole or a pharmaceutically acceptable salt thereof.

3. The method according to claim 1, wherein said compound is 4-{5-[1-(4-chloro-2,6-difluorophenoxy)-1-methylethyl]-4-methyl-4H-1,2,4-triazol-3-yl}-3-fluorobenzamide or a pharmaceutically acceptable salt thereof.

4. The method according to claim 1, wherein said compound is 4-{4-cyclopropyl-5-[1-(2,4-difluorophenoxy)-1-methylethyl]-4H-1,2,4-triazol-3-yl}-3-fluorobenzamide or a pharmaceutically acceptable salt thereof.

5. The method according to claim 1, wherein said compound is 3-(2-chloro-4-fluorophenyl)-4-methyl-5-[1-methyl-1-(2,4,6-trifluorophenoxy)ethyl]-4H-1,2,4-triazole or a pharmaceutically acceptable salt thereof.

6. The method according to claim 1, wherein said compound is 4-{5-[1-(4-chloro-2,6-difluorophenoxy)-1-methylethyl]-4-ethyl-4H-1,2,4-triazol-3-yl}benzamide or a pharmaceutically acceptable salt thereof.

7. The method according to claim 1, wherein said compound is 3-fluoro-4-{4-isopropyl-5-[1-methyl-1-(2,4,6-trifluorophenoxy)ethyl]-4H-1,2,4-triazol-3-yl}benzamide or a pharmaceutically acceptable salt thereof.

8. The method according to claim 1, wherein said compound is administered at a daily dose of 0.001 to 10 mg/kg body weight.

9. The method according to claim 1, wherein said compound is administered at a daily dose of 0.1 to 10 mg/kg body weight.

* * * * *